United States Patent [19]

Takeda

[11] Patent Number: Plant 7,170

[45] Date of Patent: Feb. 27, 1990

[54] PEACH TREE, "RUBY MAY"

[76] Inventor: Joe S. Takeda, 26729 E. Huntsman Ave., Orosi, Calif. 93647

[21] Appl. No.: 260,033

[22] Filed: Oct. 20, 1988

[51] Int. Cl.[4] ..... A01H 5/00

[52] U.S. Cl. ..... Plt./43

[58] Field of Search ..... Plt./43

[56] References Cited

U.S. PATENT DOCUMENTS

| | | | |
|---|---|---|---|
| P.P. 4,064 | 6/1977 | Minami | Plt. 43 |
| P.P. 4,827 | 2/1982 | Takanishi | Plt. 43 |
| P.P. 5,344 | 11/1984 | Spada et al. | Plt. 43 |
| P.P. 5,388 | 1/1985 | Goosen | Plt. 43 |
| P.P. 5,709 | 4/1986 | Michaelian | Plt. 43 |
| P.P. 5,839 | 12/1986 | Carbonneil | Plt. 43 |
| P.P. 6,025 | 9/1987 | Balakian | Plt. 43 |
| P.P. 6,387 | 11/1988 | Champus | Plt. 43 |

OTHER PUBLICATIONS

Brooks, R. M. et al., "Peach", *Register of New Fruit and Nut Varieties* (1972, 2nd Ed.) University of California Press, Berkeley, p. 423.

*Primary Examiner*—James R. Feyrer
*Attorney, Agent, or Firm*—Worrel & Worrel

[57] ABSTRACT

A new and distinct variety of Peach Tree which is characterized as to novelty by a date of maturity approximately May 3 through May 10 under the ecological conditions prevailing at Orosi, Calif. in the San Joaquin Valley of Central California.

1 Drawing Sheet

BACKGROUND OF THE NEW VARIETY

The present invention relates to a new and distinct variety of Peach tree, hereinafter denominated varietally as "Ruby May" and which is generally similar in its overall physical characteristics to the Springcrest Peach Tree (unpatented), of which it is a newly found scaffold mutation, but from which it is distinguished therefrom, and characterized principally as to novelty by bearing fruit which are ripe for commercial harvesting and shipment approximately May 3 through May 10 under the ecological conditions prevailing in Orosi, Calif. and which further produces fruit which have a good flavor, and excellent shipping and handling characteristics.

The Springcrest Peach Tree (unpatented) was developed by the U.S. Department of Agriculture, and is well known for producing a highly attractive, early ripening, semi-freestone peach of good quality and excellent market acceptance. As with all fruits, the time of harvesting peaches greatly influences the prices which such produce will bring on the open market. As a general matter, the earlier that a particular fruit variety can be marketed with other varieties it is mostly similar to, then the higher the price it can bring on the market. This is the case with the instant variety of Peach Tree, "Rudy May".

ORIGIN AND ASEXUAL REPRODUCTION OF THE NEW VARIETY

The present variety of Peach Tree, "Ruby May" was discovered as a scaffold mutation growing on a Springcrest Peach Tree (unpatented) within the cultivated area of the inventor's orchard which is located on Road 136 in Orosi, Calif. The discovery, which occurred in 1985 during routine orchard operations, was marked for subsequent observation. During the winter of 1986 the inventor asexually reproduced the new variety of peach by removing buds from the scaffold mutation and by budding them into test trees which are located in the same orchard which is located on Road 136 in Orosi, Calif. These test trees have been continually observed by the inventor and it has subsequently been determined that the progeny produced by these budded test trees possessed the same distinctive characteristics as the original scaffold mutation.

BRIEF DESCRIPTION OF THE DRAWINGS

The accompanying drawing is a color photograph of a characteristic twig bearing typical leaves, several mature fruit showing their external coloration sufficiently matured for harvesting and shipment, one fruit of the subject variety dissected in the axial plane to illustrate the flesh characteristics, and several stones all of the subject variety.

DETAILED DESCRIPTION

Referring more specifically to the pomological details of this new and distinct variety of peach tree, the following has been observed under the ecological conditions prevailing at the orchard of the inventor which is located in Orosi, Calif. All major color code designations are by reference to the Dictionary of Color by Maerz and Paul, Second Edition, 1950. Common color names are also employed occasionally.

TREE

Size:
- *Generally.*—Average.

Figure: Spreading, depending upon pruning practices.
Productivity: Productive.
Regularity of bearing: Regular.
Trunk:
- *Size.*—Average.
- *Surface texture.*—Medium, as compared with other common peach cultivars.

Branches:
- *Size.*—Average.
- *Surface texture.*—Average.
- *Color.*—Grey, (Page 53, Plate 15, C-5).

Lenticels:
- *Numbers.*—Average.
- *Size.*—Medium.
- *Average length.*—Approximately 4–6 mm.

*Average width.*—Approximately 1–2 mm.

LEAVES

Size:
*Generally.*—Average.
*Average length.*—Approximately 115–130 mm.
*Average width.*—Approximately 30–33 mm.
Shape:
*Generally.*—Lanceolate.
Color — Upwardly disposed surface: Dark Green, (Page 71, Plate 24, L-5).
Color — Downwardly disposed surface: Pale Green, (Page 69, Plate 23, L-6).
Marginal form:
*Generally.*—Finely serrate.
Petiole:
*Length.*—Approximately 11–12 mm.
*Thickness.*—Approximately 2 mm.
Stem glands:
*Numbers.*—Two.
*Arrangement.*—Considered opposite.
*Size.*—Small.
*Type.*—Globose.
Stem glands:
*Color.*—Red; the color is not particularly distinctive, however.
Stipules:
*Generally.*—Not evident.

FLOWER BUDS

Generally: The flower buds of the subject variety are quite similar to the flower buds observed on the Springcrest Peach Tree (unpatented). They are, however, not particularly distinctive of the subject variety.
Size:
*Generally.*—Large.
Shape:
*Obtuse, and plump.*
Surface characterictics—Pubescent.

FLOWERS

Date of bloom: In 1988, full bloom was achieved on March 5.
Size:
*Generally.*—Large.
*Average diameter.*—Approximately 25 mm.
Petal color — upwardly disposed surface: Pink, (Page 121, Plate 49, G-7).
Petal color—downwardly disposed surface: A lighter pink, (Page 121, Plate 49, E-6).
Pistils:
*Numbers.*—One.
Stamens:
*Numbers.*—Variable, 44–48 stamens may be observed.

FRUIT

Maturity when described: Ripe for harvesting and shipment approximately May 3 through May 10 under the ecological conditions prevailing in the San Joaquin Valley of Central California.
Size:
*Uniformity.*—Uniform.
*Average diameter in the axial plane.*—Approximately 56–58 mm.
*Average diameter transverse in the suture plane.*—*Approximately* 57–59 mm.
*Average diameter transverse and at right angles to the suture plane.*—Approximately 51–53 mm.
Form:
*Uniformity.*—Uniform.
Symmetry: Asymmetrical; the subject variety is considered globose and has unequal sides.
Suture:
*Generally.*—The suture appears as a smooth yet distinct line which extends from the base to the pistil point.
*Length.*—Approximately 75–80 mm.
Ventral surface:
*Shape.*—Rounded.
Stem cavity:
*Shape.*—Rounded, and elongated in the suture plane.
*Length.*—Approximately 21–22 mm.
*Width.*—Approximately 14–15 mm.
*Depth.*—Approximately 7 mm.
Apex:
*Shape.*—Rounded.
Pistil:
*Position.*—Variable, usually oblique to the fruit axis.
Stem:
*Length.*—Approximately 9–10 mm.
*Caliper.*—Approximately 3–4 mm.
Skin:
*Thickness.*—Average.
*Surface texture.*—Normal.
Tendency to crack: Not observed.
Ground color: Yellow, (Page 45, Plate 11, K-2).
Blush color: Red, (Page 37, Plate 7, J-4).
Pubescence: Slight.
Flesh:
*Color.*—Yellow, (Page 45, Plate 11, K-2).
Surface of pit cavity: Yellow, (Page 45, Plate 11, K-2).
Color of pit well: Substantially similar to the surface of the pit cavity.
Amygdalin: Present.
Juice Production: Juicy.
Flavor: Considered subacid.
Aroma: Distinct.
Flesh texture: Average.
Fibers: Present and fine.
Ripening: Even.
Eating quality: Good.

STONE

Attachment: Considered semi-freestone.
Fibers:
*Length.*—Long.
Size:
*Average length.*—Approximately 32–35 mm.
*Width.*—Approximately 22–25 mm.
*Thickness.*—Approximately 17–19 mm.
Form:
*Generally.*—Oval, and beaked.
*Ventral edge—shape.*—Thin, and having no wing.
*Dorsal edge—shape.*—A deep broad groove appears over the entire length of the dorsal edge.
Base: Oblique.
Sides:
*Generally.*—Equal and irregularly furrowed near the apex. Some pits appear near the base.
Ridges:
*Shape.*—Rounded.
Position of grooves: Appearing near the base.

Dry color: Brown; this color is not particularly distinctive of the variety, however.

Splitting tendency: Not observed.

Fruit use: Fresh market peach for both local and long distance markets.

Keeping quality: Average.

Shipping quality: Good.

Although the new variety of peach tree possesses the described characteristics when grown under the ecological conditions prevailing in Orosi, Calif., in the Central part of the San Joaquin Valley of California, it is to be understood that variations of the usual magnitude and characteristics incident to changes in growing conditions, fertilization, pruning and pest control are to be expected.

Having thus described and illustrated my new variety of peach tree, what is claimed as new and desired to be secured by Letters Patent is:

1. A new and distinct variety of Peach Tree substantially as illustrated and described and which is somewhat similar to the Springcrest Peach Tree (unpatented) from which it was derived as a scaffold mutation, but from which it is distinguished therefrom and characterized 'principally as to novelty by bearing fruit which are ripe for commercial harvesting and shipment approximately May 3 through May 10 at Orosi, Calif., and which further produces a semi-freestone fruit which has a good flavor and noteworthy handling characteristics.

* * * * *

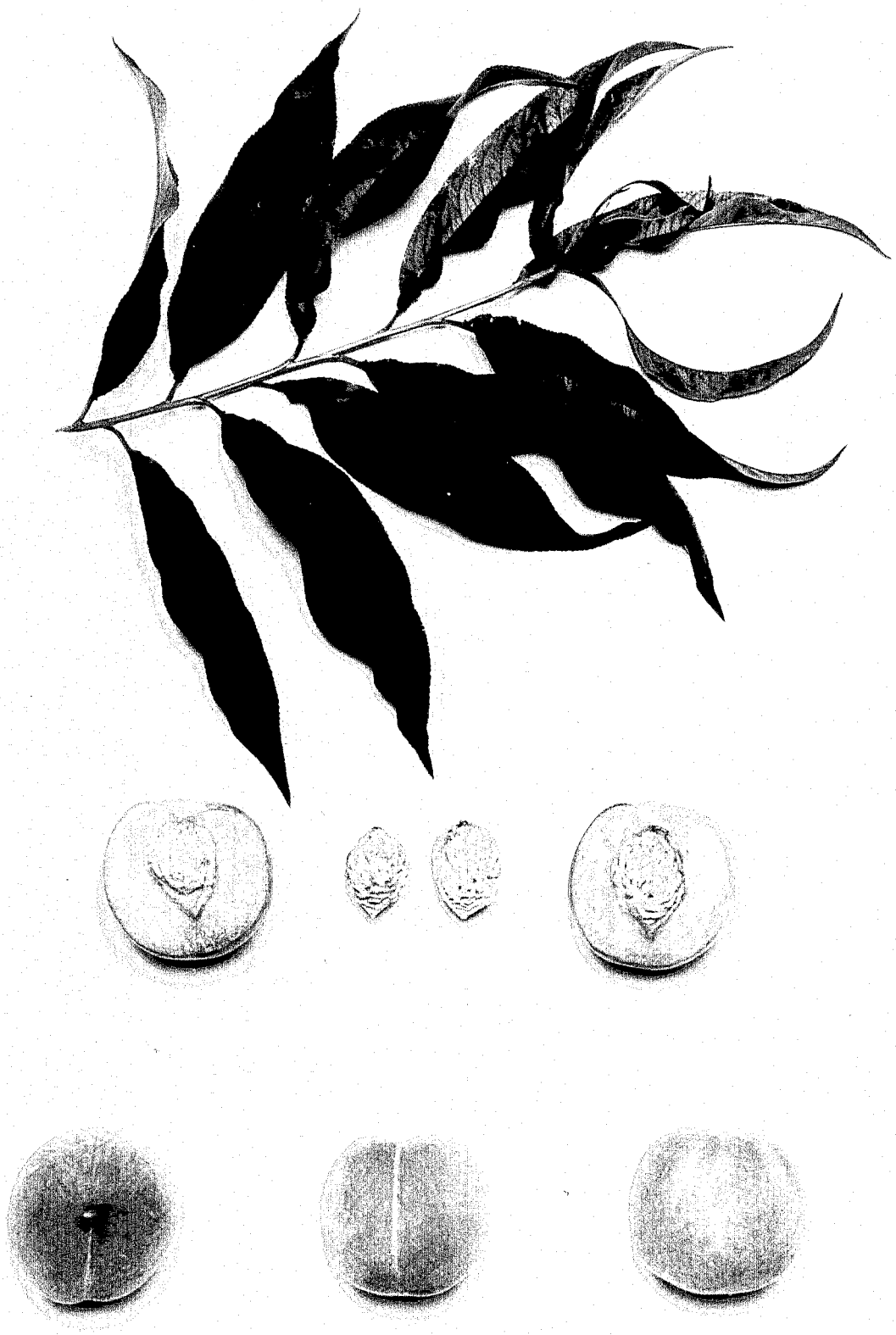

UNITED STATES PATENT AND TRADEMARK OFFICE

CERTIFICATE OF CORRECTION

PATENT NO. : PP 7,170

DATED : February 27, 1990

INVENTOR(S) : Joe S. Takeda

It is certified that error appears in the above-identified patent and that said Letters Patent is hereby corrected as shown below:

Column 1, Line 27

Delete "Rudy" and Insert ---Ruby---

Signed and Sealed this

Twenty-sixth Day of March, 1991

*Attest:*

*Attesting Officer*

HARRY F. MANBECK, JR.

*Commissioner of Patents and Trademarks*